(12) United States Patent
Sung et al.

(10) Patent No.: US 11,420,199 B2
(45) Date of Patent: Aug. 23, 2022

(54) LIQUID PROCESSING MODULE, LIQUID TESTING SYSTEM AND TESTING METHOD

(71) Applicant: WISTRON CORP., New Taipei (TW)

(72) Inventors: Chen-An Sung, New Taipei (TW);
Chih Chen Chang, New Taipei (TW);
Kai-Sheng Chen, New Taipei (TW)

(73) Assignee: WISTRON CORP., New Taipei (TW)

( * ) Notice: Subject to any disclaimer, the term of this patent is extended or adjusted under 35 U.S.C. 154(b) by 1016 days.

(21) Appl. No.: 16/057,439

(22) Filed: Aug. 7, 2018

(65) Prior Publication Data

US 2019/0291098 A1 Sep. 26, 2019

(51) Int. Cl.
*B01L 3/00* (2006.01)
*C12N 15/10* (2006.01)
*G01N 1/14* (2006.01)
*G01N 33/53* (2006.01)

(52) U.S. Cl.
CPC .......... *B01L 3/502* (2013.01); *C12N 15/1013* (2013.01); *B01L 2300/045* (2013.01); *B01L 2300/14* (2013.01); *B01L 2400/0475* (2013.01); *B01L 2400/06* (2013.01)

(58) Field of Classification Search
CPC ............... B01L 3/502; B01L 2300/045; B01L 2300/14; B01L 2300/0475; B01L 2300/06
See application file for complete search history.

(56) References Cited

FOREIGN PATENT DOCUMENTS

TW 201326576 A 7/2013
TW I479087 B 4/2015

OTHER PUBLICATIONS

Chinese Office Action issued in corresponding application No. 201810330692.4, dated Jun. 24, 2021.

*Primary Examiner* — Christopher Adam Hixson
(74) *Attorney, Agent, or Firm* — Maschoff Brennan (57) ABSTRACT

The disclosure is related to a liquid processing module, a liquid testing system and a testing method. The liquid processing module includes a base, a first valve and at least one negative pressure generator. The base has a first groove and at least one first opening. The first opening is connected to the first groove. The first valve is slidably located in the first groove. The negative pressure generator is configured to generate or remove negative pressure at the first opening in response to the first opening and the first groove being connected with each other.

20 Claims, 10 Drawing Sheets

LIQUID PROCESSING MODULE, LIQUID TESTING SYSTEM AND TESTING METHOD

CROSS-REFERENCE TO RELATED APPLICATIONS

This non-provisional application claims priority under 35 U.S.C. § 119(a) on Patent Application No(s). 107109688 filed in Taiwan, R.O.C. on Mar. 21, 2018, the entire contents of which are hereby incorporated by reference.

TECHNICAL FIELD

The disclosure relates to a liquid processing module and a liquid testing system, more particularly to a liquid processing module having negative pressure generator and a test device having the liquid processing module.

The disclosure also relates to a testing method, more particularly to a testing method that utilizes the liquid processing module having the negative pressure generator to perform testing.

BACKGROUND

Nucleic acid analysis is an important method in biomedical research and clinical diagnosis, thus, nucleic acid separation and extraction technologies have developed rapidly. How to combine related technologies to effectively extract and separate high purity nucleic acid from a biological sample or clinic sample becomes a development goal in this field. For example, after microparticles (e.g., magnetic beads) having specific functional groups absorb nucleic acids in a mixed liquid of a sample in a specific manner, a magnetic controlling device (e.g., magnetic) cooperated with the magnetic beads provides a magnetic force or a magnetic field to attract and move the magnetic beads in order to perform steps of reaction, wash, extraction and so on. This type of nucleic acid extraction method is also called a "magnetic bead type nucleic acid extraction method".

In a conventional magnetic bead type nucleic acid extraction method, a lysed sample, a mixed liquid of lysate mixture and a specific amount of magnetic beads are added into a test tube. At this point, the nucleic acids in the sample are released in the mixed liquid, such that the magnetic beads can be attached on the nucleic acids. After a magnet absorbs the magnetic beads with the nucleic acids, the solution in the test tube is sucked out. Then, after a first buffer solution is added into the test tube to infiltrate and rinse the impurities on the magnetic beads which are attached with the nucleic acids, and the magnetic beads with the nucleic acids are attracted by a magnet, the solution in the test tube is sucked out; continue to inject the second buffer solution into the tube and further rinse the impurities on the magnetic beads which are attached with the nucleic acids, and after the magnetic beads which are attached with the nucleic acids are attracted by the magnet, the solution in the tube is sucked out. Also, after performing the first ground of magnetic bead nucleic acid extractions, the next ground of magnetic bead nucleic acid extractions is performed.

SUMMARY OF THE INVENTION

One embodiment of the disclosure provides a liquid processing module. The liquid processing module includes a base, a first valve and at least one negative pressure generator. The base has a first groove and at least one first opening. The first opening is connected to the first groove. The first valve is slidably located in the first groove. The negative pressure generator is configured to generate or remove negative pressure at the first opening in response to the first opening and the first groove being connected with each other.

Another embodiment of the disclosure provides a testing method. The testing method includes opening a second valve to open a fourth opening, injecting a first liquid into a liquid storage tank through the fourth opening, generating negative pressure at the fourth opening, closing the second valve to close the fourth opening, opening a first valve to open a first opening, sucking a second liquid located in the liquid storage tank through the first opening, generating negative pressure at the first opening and closing the first valve to close the first opening.

Still another embodiment of the disclosure provides a liquid testing system. The liquid testing system includes a testing stand and a liquid processing module. The liquid processing module is replaceably mounted on the testing stand. The liquid processing module includes a base, at least one first valve and at least one negative pressure generator. The base has a first groove and at least one first opening. The first opening is connected to the first groove. The first valve is slidably located in the first groove. The negative pressure generator is configured to generate or remove negative pressure at the first opening in response to the first opening and the first groove being connected with each other.

BRIEF DESCRIPTION OF THE DRAWINGS

The present disclosure will become better understood from the detailed description given herein below and the accompanying drawings which are given by way of illustration only and thus are not intending to limit the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
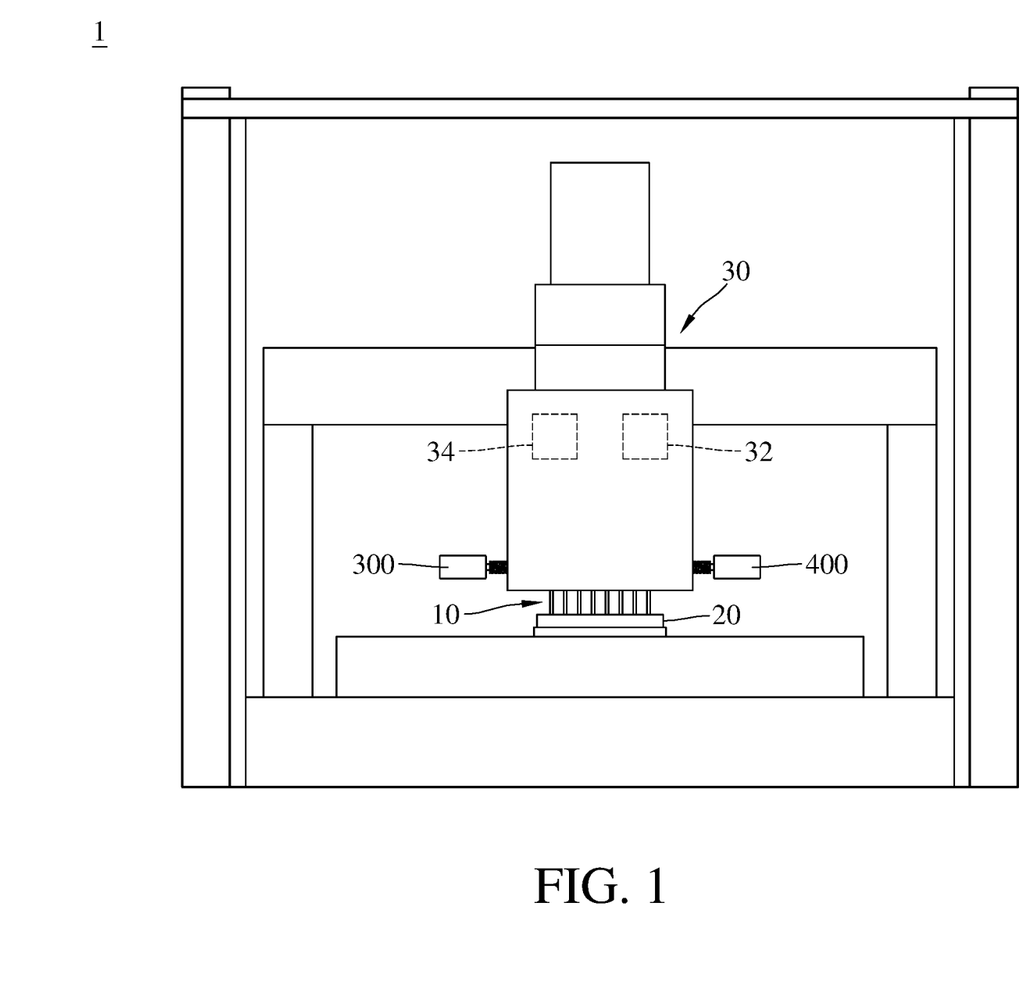
FIG. 1 is a schematic view of a liquid testing system according to a first embodiment of the disclosure with a carrier.
Figure 2:
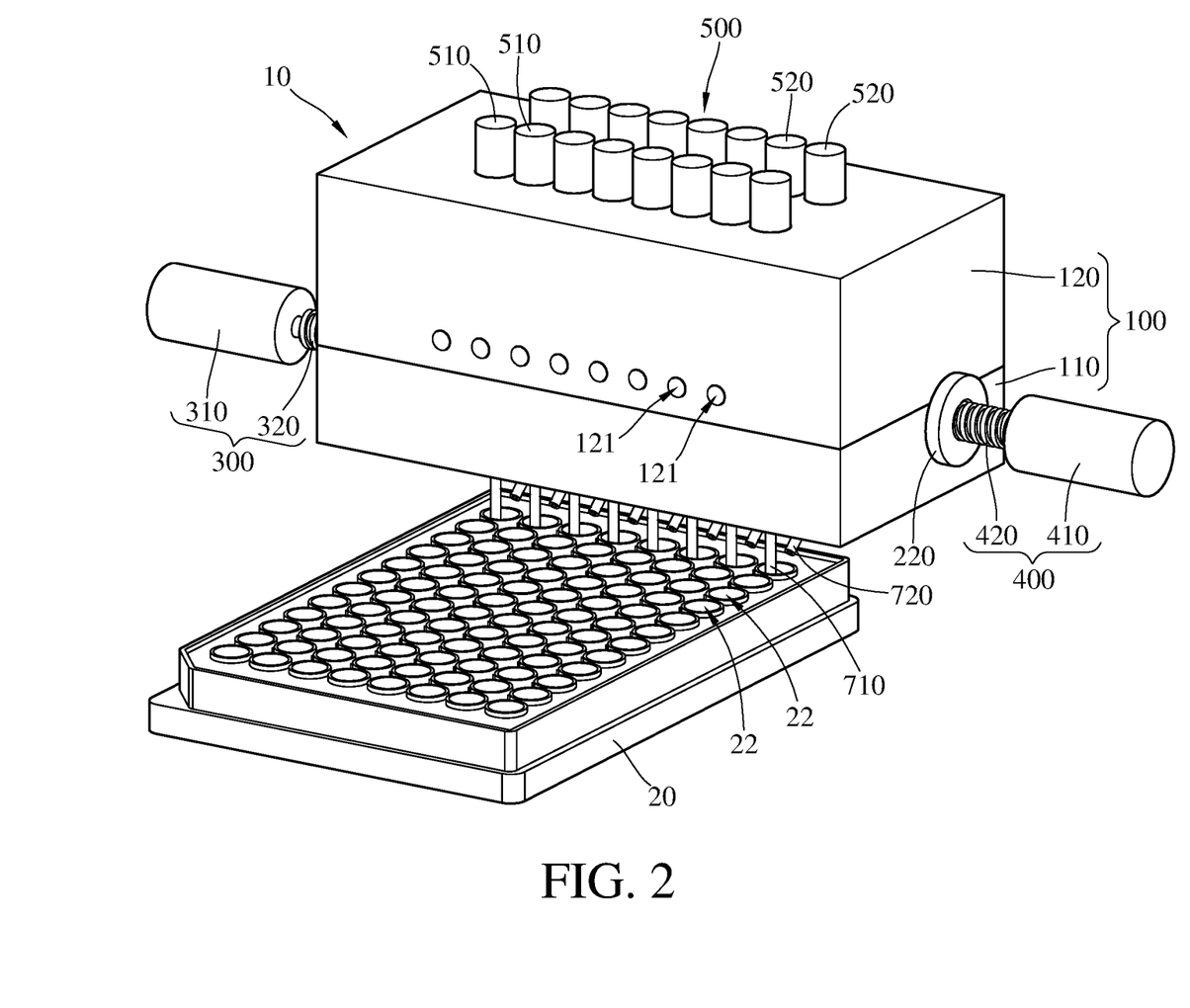
FIG. 2 is a perspective view of a liquid processing module and the carrier in FIG. 1.
Figure 3:
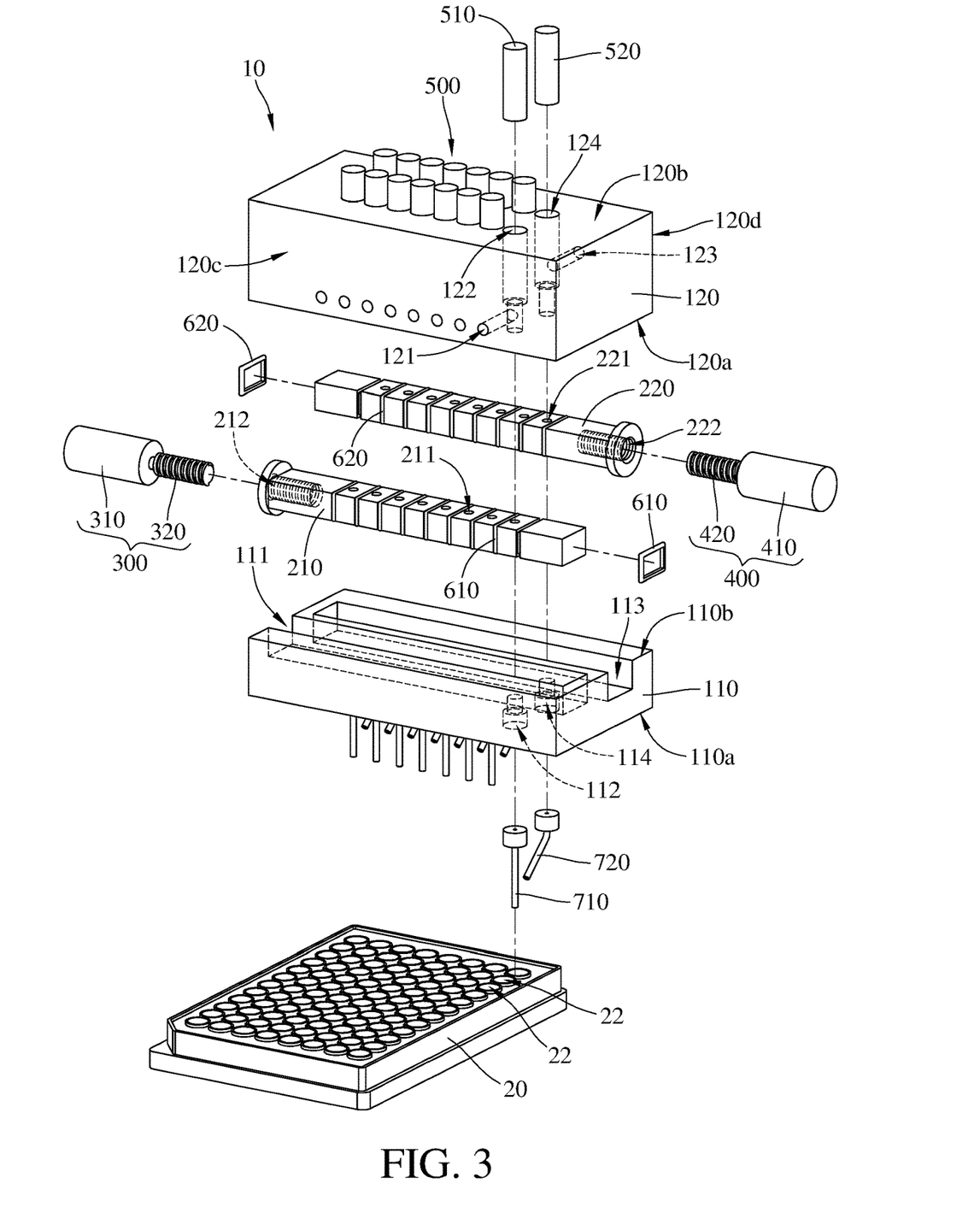
FIG. 3 is an exploded view of the liquid processing module and the carrier in FIG. 2.
Figure 4:
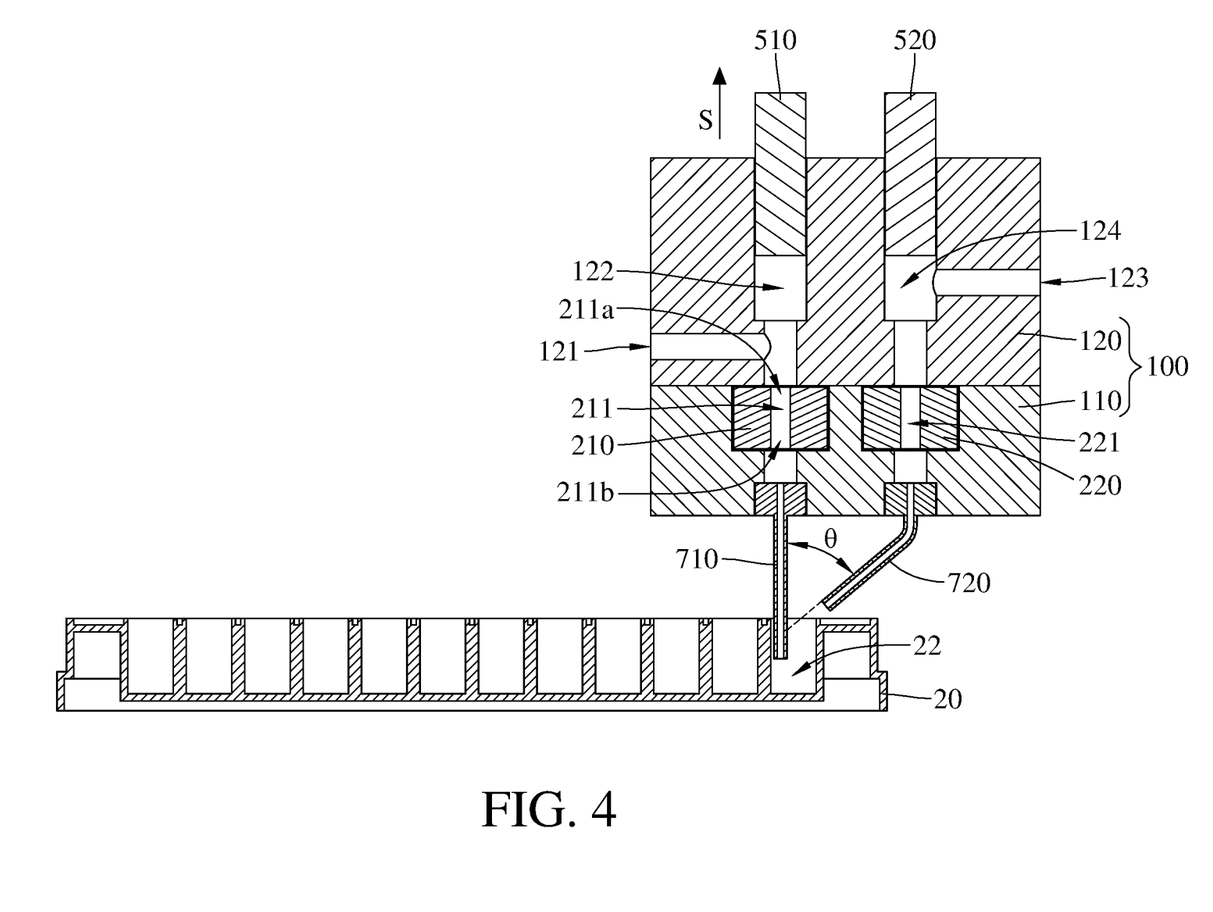
FIG. 4 is a cross-sectional view of the liquid processing module and the carrier in FIG. 2.

Please refer to FIG. 1 to FIG. 4. FIG. 1 is a schematic view of a liquid testing system according to a first embodiment of the disclosure being cooperated with a carrier. FIG. 2 is a perspective view of a liquid processing module and the carrier in FIG. 1. FIG. 3 is an exploded view of the liquid processing module and the carrier in FIG. 2. FIG. 4 is a cross-sectional view of the liquid processing module and the carrier in FIG. 2.

This embodiment provides a liquid testing system 1. The liquid testing system 1 includes a liquid processing module 10 and a testing stand 30. The liquid processing module 10 is mounted on the testing stand 30. The liquid processing module 10 is, for example, replaceable, thus the liquid processing module 10 is easily to be cleaned and maintained. There may be a three-axis movement apparatus mounted on the testing stand 30 for moving the liquid processing module 10 in three directions. In addition, there may be a liquid suction pump 32 and a liquid delivering pump 34 which are mounted on the testing stand 30. The liquid suction pump 32 and the liquid delivering pump 34 are respectively configured to suck liquid from and inject liquid into liquid storage tanks 22 of the carrier 20 via the liquid processing module 10.

In detail, the liquid processing module 10 includes a base 100, a first valve 210, a second valve 220, a first driving component 300, a second driving component 400 and a negative pressure generator 500.

The base 100 includes a lower part 110 and an upper part 120. The lower part 110 has a first surface 110a, a second surface 110b, a first groove 111, a plurality of first openings 112, a second groove 113 and a plurality of fourth openings 114. The second surface 110b is opposite to the first surface 110a. When the base 100 is located above the carrier 20, the first surface 110a is closer to the carrier 20 than the second surface 110b. The first groove 111 and the second groove 113 are located on the second surface 110b, and the second groove 113 and the first groove 111 are not connected to each other. The first openings 112 and the fourth openings 114 are located on the first surface 110a and respectively arranged along a straight line. The first openings 112 are connected to the first groove 111, and the fourth openings 114 are connected to the second groove 113.

In this embodiment, the fourth openings 114 and the first openings 112 are not restricted in a straight line arrangement. In addition, the quantity of the fourth openings 114 equals to the quantity of the first openings 112. However, the present disclosure is not limited thereto. In some other embodiments, the fourth openings 114 and the first openings 112 both are plural but may be different in quantity; or the base may only have one fourth opening 114 and one first opening 112. Furthermore, in this embodiment, the disconnection between the second groove 113 and the first groove 111 can prevent liquid sucked from the first opening 112 and liquid injected from the fourth opening 114 from being mixed and contaminated with each other. However, if there is no contamination between liquid sucked from the first opening 112 and liquid injected from the fourth opening 114, the first groove 111 and the second groove 113 may be connected to each other.

The upper part 120 has a third surface 120a, a fourth surface 120b, a fifth surface 120c, a sixth surface 120d, a plurality of second openings 121, a plurality of first chambers 122, a plurality of third openings 123 and a plurality of second chambers 124. The fourth surface 120b is opposite to the third surface 120a. When the base 100 is located above the carrier 20, the third surface 120a is closer to the carrier 20 than the fourth surface 120b. The fifth surface 120c and the sixth surface 120d are located between the third surface 120a and the fourth surface 120b, and the fifth surface 120c is opposite to the sixth surface 120d. The first chambers 122 and the second chambers 124 are located on the fourth surface 120b. The second openings 121 are located on the fifth surface 120c, and the third openings 123 are located on the sixth surface 120d. The upper part 120 is stacked on the second surface 110b of the lower part 110 via the third surface 120a, and the upper part 120 covers the first groove 111 and the second groove 113. In addition, the second openings 121 and the first chambers 122 are respectively connected to the first openings 112 through the first groove 111, and the third openings 123 and the second chambers 124 are respectively connected to the fourth openings 114 through the second groove 113.

In this embodiment, the upper part 120 covers the first groove 111 and the second groove 113 which are located on the second surface 110b of the lower part 110, but the present disclosure is not limited thereto. In some other embodiments, the first groove and the second groove may be located on the third surface of the upper part; that is, the lower part may cover the first groove and the second groove located on the third surface of the upper part.

Moreover, the base 100 is divided into the upper part 120 and the lower part 110, but the present disclosure is not limited thereto. In some other embodiments, the base may be divided into a left part and a right part. In addition, the base may be divided into three pieces, or according to actual requirements such as maintenance, cleaning or only requiring a part of functions.

In this embodiment, the second openings 121 are connected to the liquid suction pump 32 so that the liquid suction pump 32 is able to suck liquid via the first openings 112, and the liquid flowing through the first openings 112 will flow toward the second openings 121 through the first groove 111. The third openings 123 are connected to the liquid delivering pump 34 so that the liquid delivering pump 34 is able to inject liquid via the third openings 123, and the liquid flowing through the third openings 123 will flow toward the fourth openings 114 through the second groove 113.

Figure 6:
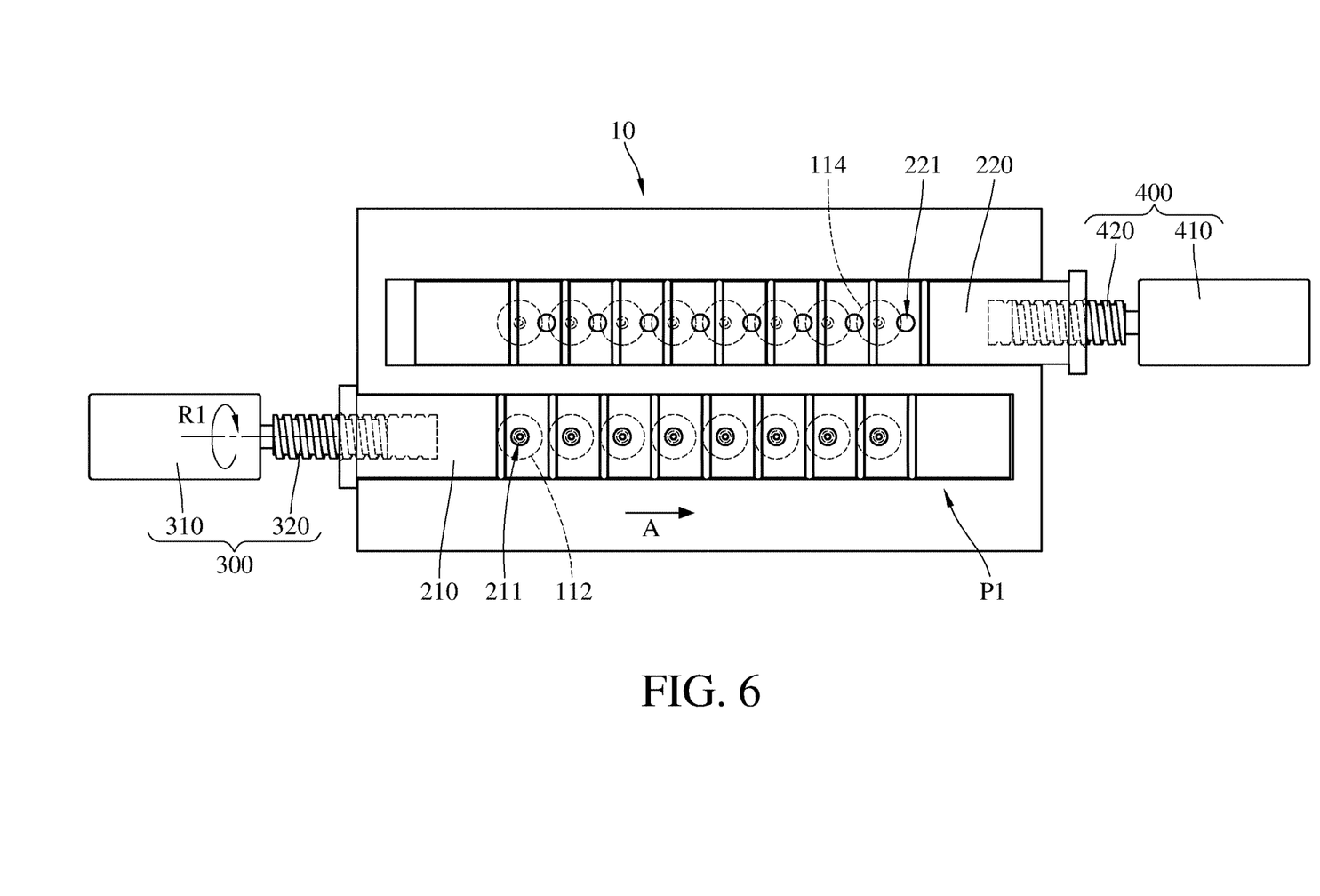
FIG. 6 to FIG. 10 are schematic views showing the liquid suction operation of the liquid processing module in FIG. 2.
Figure 9:
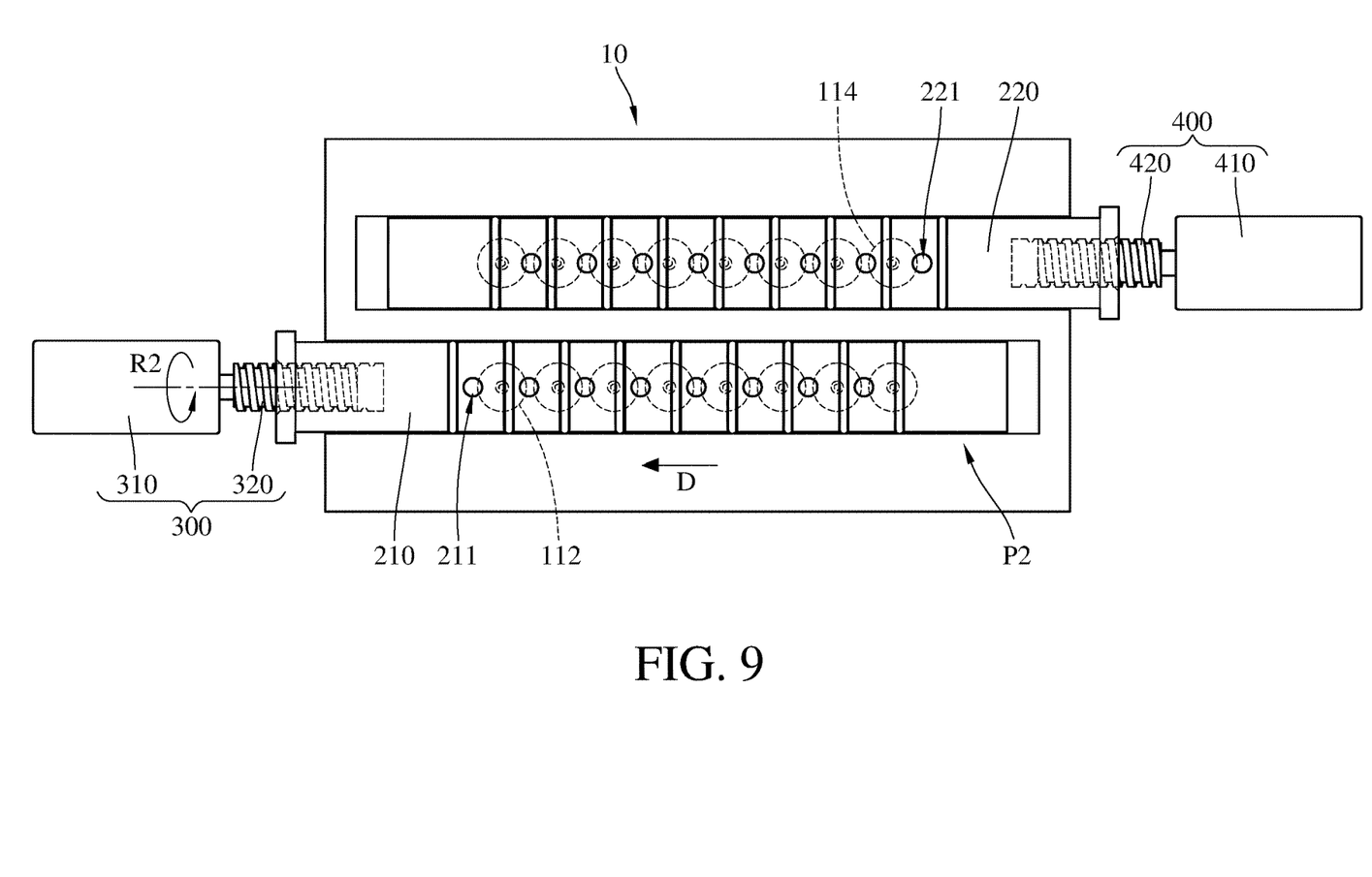

The first valve 210 has a plurality of first channels 211, and each of the first channels 211 has two openings 211a and 211b. The openings 211a respectively correspond to the second openings 121, and the openings 211b respectively correspond to the first openings 112. The first valve 210 is located in the first groove 111 and slidable between a first state P1 (e.g., as shown in FIG. 6) and a second state P2 (e.g., as shown in FIG. 9). In response to the first valve 210 being in the first state P1, the first openings 112 are respectively connected to the second openings 121 through the first channels 211. In response to the first valve 210 being in the second state P2, the first openings 112 are not connected to the second openings 121. That is, when the first valve 210 is in the second state P2, the first valve 210 blocks passages between the first openings 112 and the second openings 121 in order to prevent liquid flowing toward the second openings 121 from flowing back to the first openings 112.

The second valve 220 has a plurality of second channels 221. The second valve 220 is located in the second groove 113 and slidable between a third state (e.g., similar to the first state) and a fourth state (e.g., as shown in FIG. 6). In response to the second valve 220 being in the third state, the fourth openings 114 are respectively connected to the third openings 123 through the second channels 221. In response to the second valve 220 being in the fourth state, the fourth openings 114 are not connected to the third openings 123. That is, when the second valve 220 is in the fourth state, the second valve 220 blocks passages between the fourth openings 114 and the third openings 123 in order to prevent liquid flowing toward the second channel 221 from flowing to the fourth openings 114.

Figure 8:
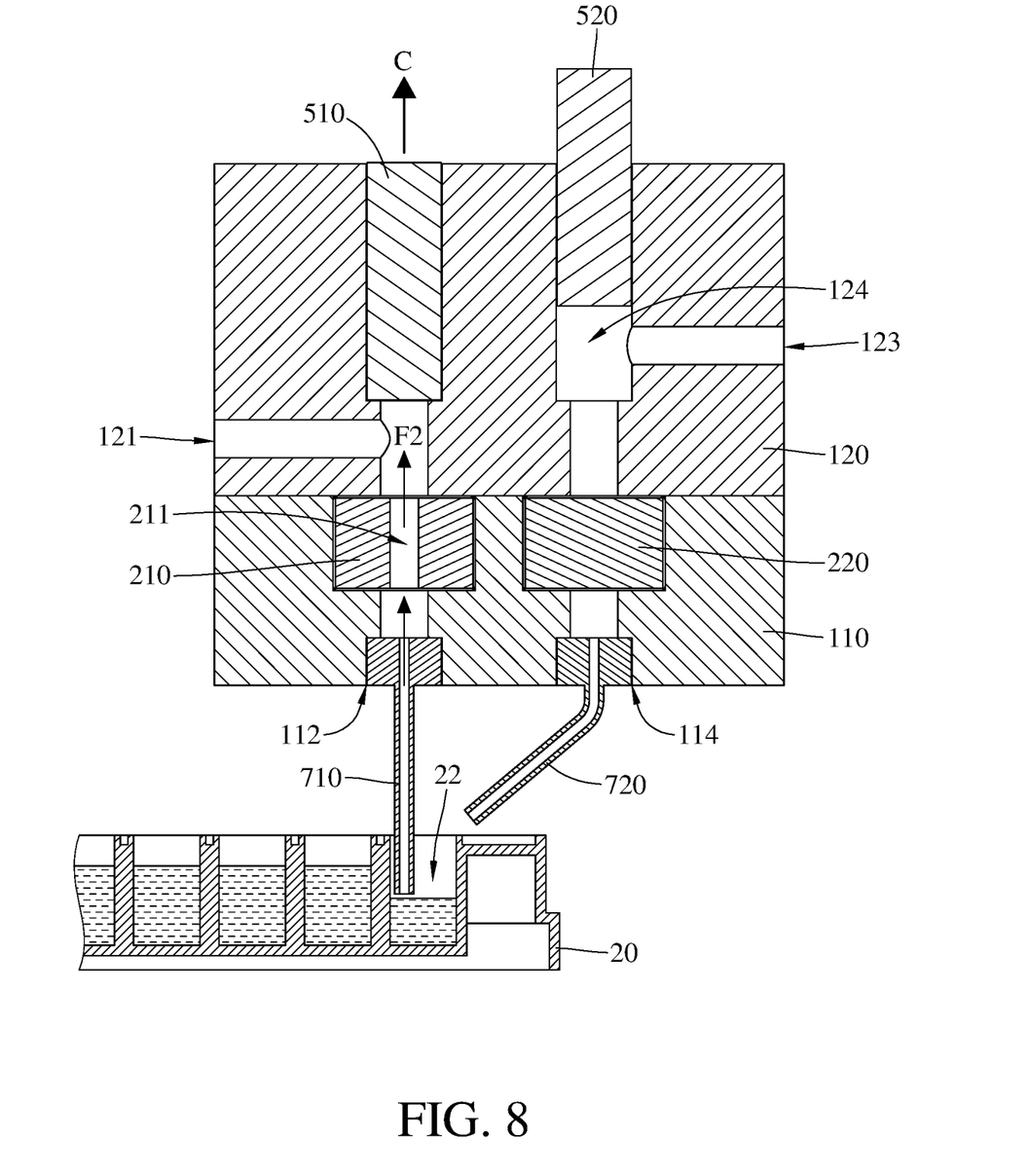

The negative pressure generator 500 includes a plurality of first pistons 510 and a plurality of second pistons 520. The first pistons 510 are respectively slidably located in the first chambers 122 so as to respectively generate or remove negative pressure at the first openings 112. In detail, as shown in FIG. 4, when the first piston 510 is moved away from the first opening 112 in a direction S, the space occupied by air in the first chamber 122 is gradually increased, but the amount of air is still the same, such that a pressure in the first chamber 122 becomes lower than ambient pressure, thereby generating negative pressure at the first opening 112. On the other hand, when the first piston 510 is moved toward a position close to the first opening 112 (e.g., as shown in FIG. 8), the pressure in the first chamber 122 is balance to ambient pressure, such that the negative pressure is removed. In the same manner, the second pistons 520, which are respectively slidably located in the second chambers 124, are able to generate or remove negative pressure at the fourth openings 114.

In addition, the first pistons 510 and the second pistons 520 are moved by, for example, gas pressure control, but the present disclosure is not limited thereto. In some other embodiments, the first pistons 510 and the second pistons 520 may be moved manually or electronically.

The liquid processing module 10 further includes a plurality of first seal rings 610, a plurality of second seal rings 620, a plurality of first pipes 710 and a plurality of second pipes 720.

The first seal rings 610 are, for example, made of rubber. The first seal rings 610 are sleeved on the first valve 210, and two of the first seal rings 610 adjacent to each other are respectively located on two opposite sides of each first channel 211 so as to prevent the first channels 211 from connecting to each other.

The second seal rings 620 are, for example, made of rubber. The second seal rings 620 are sleeved on the second valve 220, and two of the second seal rings 620 adjacent to each other are respectively located on two opposite sides of each of the second channels 221 so as to prevent the second channels 221 from connecting to each other.

The first pipes 710 are respectively mounted on the first openings 112 of the lower part 110. The second pipes 720 are respectively mounted on the fourth openings 114 of the lower part 110. In addition, as shown in FIG. 3 and FIG. 4, a length that the first pipe 710 protrudes from the lower part 110 is greater than a length that the second pipe 720 protrudes from the lower part 110, and the second pipe 720 and the first pipe 710 have an acute angle θ therebetween. In this embodiment, the first pipe 710 is vertical to the lower part 110, and the second pipe 720 is inclined to the lower part 110. Therefore, the second pipe 720 and the first pipe 710 can be pointed at the same liquid storage tank 22 even when a distance between the fourth opening 114 and the first opening 112 is larger than the opening width of the liquid storage tank 22. That is, in the case that distance between the fourth opening 114 and the first opening 112 is larger than the opening width of the liquid storage tank 22, sucking and injecting liquid can be performed without moving the liquid processing module 10. However, the present disclosure is not limited thereto. In some other embodiments, when the opening width of the liquid storage tank is greater than the distance between the fourth opening and the first opening, the second pipe may be a vertical pipe as the first pipe.

Figure 5:
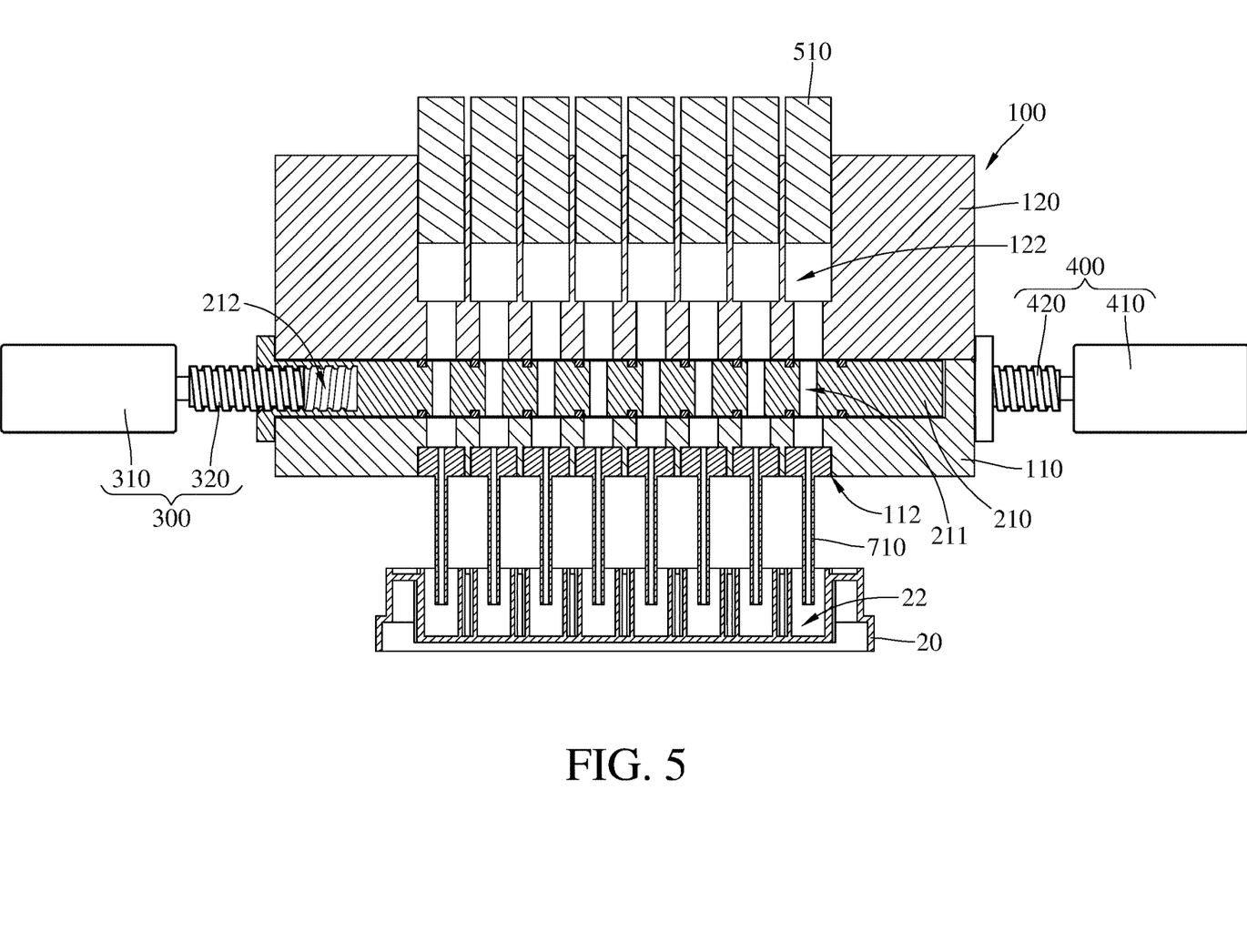
FIG. 5 is another cross-sectional view of the liquid processing module and the carrier in FIG. 2.

In addition, the first valve 210 and the second valve 220 can be moved with respect to the base 100 by, for example, an electrical manner. In detail, please refer to FIG. 2 and FIG. 5. FIG. 5 is another cross-sectional view of the liquid processing module and the carrier in FIG. 2. The first valve 210 and the second valve 220 respectively have a first assembling part 212 and a second assembling part 222. Each of the first assembling part 212 and the second assembling part 222 has internal threads. The first driving component 300 includes a first driving motor 310 and a first stud 320. The first stud 320 is rotatably mounted on the first driving motor 310, and the first stud 320 is screwed to the first assembling part 212, such that the first driving motor 310 is able to drive the first valve 210 to slide with respect to the lower part 110. The second driving component 400 includes a second driving motor 410 and a second stud 420. The second stud 420 is rotatably mounted on the second driving motor 410, and the second stud 420 is screwed to the second assembling part 222, such that the second driving motor 410 is able to drive the second valve 220 to slide with respect to the lower part 110.

It is noted that, in this embodiment, the first valve 210 and the second valve 220 are driven by an electrical manner, but the present disclosure is not limited thereto. In some other embodiments, the first valve 210 and the second valve 220 may be driven by oil pressure or a manual manner.

Then, a testing method that applies the aforementioned liquid processing module 10 is described in the following paragraphs.

Firstly, the second valve 220 is opened so as to open the fourth openings 114. Then, a first liquid is injected into the liquid storage tanks 22 through the fourth openings 114. The first liquid is, for example, lysate, washing liquid or eluent. Then, negative pressure is generated at the fourth openings 114. Then, the second valve 220 is closed so as to close the fourth openings 114. Then, the first valve 210 is opened so as to open the first openings 112. A second liquid is sucked from the liquid storage tanks 22 through the first openings 112. The second liquid is, for example, purified nucleic acids or processed wasted liquid. Then, negative pressure is generated at the first openings 112. Then, the first valve 210 is closed so as to close the first openings 112. Then, the liquid processing module 10 is moved to next testing position.

Since the operations of sucking and injecting liquid are similar to each other, the following paragraphs only illustrate the operation of sucking liquid. Please refer to FIG. 6 to FIG. 10. FIG. 6 to FIG. 10 are schematic views showing the liquid suction operation of the liquid processing module in FIG. 2.

Figure 7:
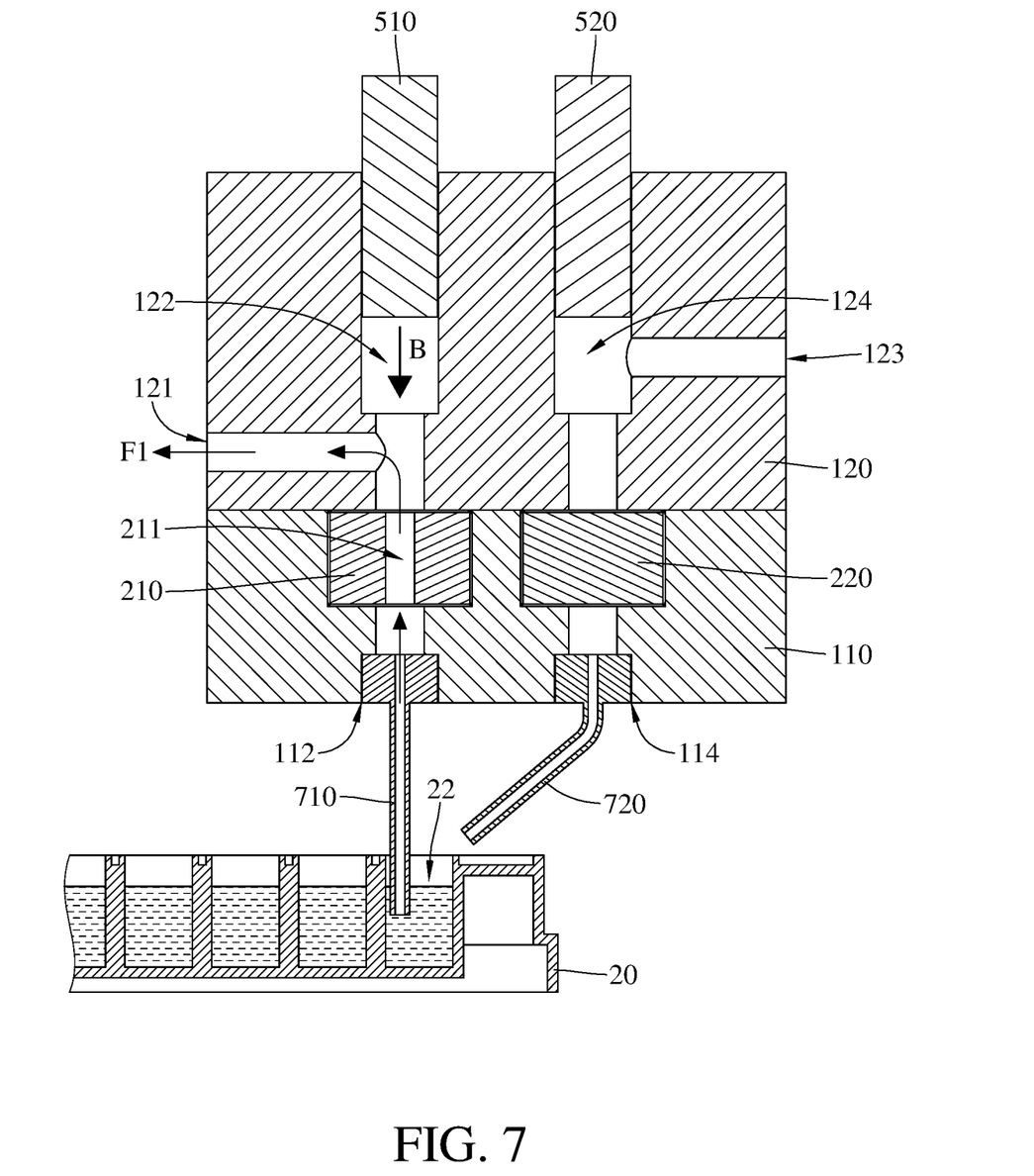

Firstly, as shown in FIG. 6, the first stud 320 is rotated in a direction R1 by being driven by the first driving motor 310. Then, the first valve 210 is moved in a direction A by being driven by the first stud 320, such that the first channels 211 of the first valve 210 are respectively aligned with the first openings 112 to allow the first openings 112 to connect to the second openings 121 (e.g., as shown in FIG. 2). Then, as shown in FIG. 7, the first pistons 510 are moved downward in a direction B, and the liquid suction pump 32 which is connected to the second openings 121 is activated to suck liquid in the liquid storage tanks 22 so as to force the liquid to flow toward the second openings 121 in a direction F1.

Figure 10:
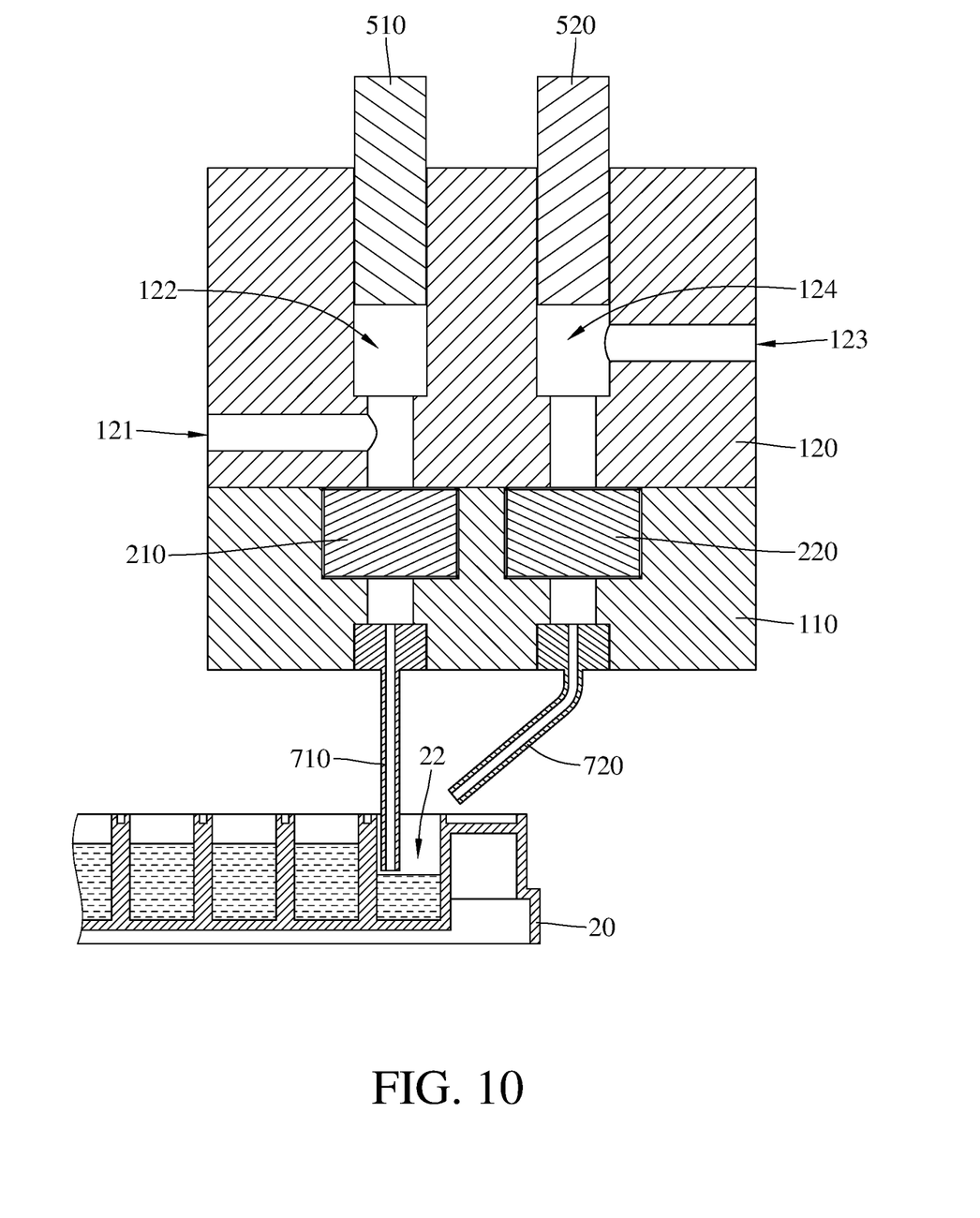

After the liquid suction is finished, as shown in FIG. 8, the first pistons 510 are moved upward in a direction C so as to create negative pressure at the first openings 112, such that the remaining liquid in the first pipes 710 or the first channels 211 is sucked in a direction F2. Then, as shown in FIG. 9 and FIG. 10, the first stud 320 is rotated in a direction R2 by being driven by the first driving motor 310. Then, the first valve 210 is moved in a direction D by being driven by the first stud 320, such that the first channels 211 of the first valve 210 are respectively misaligned with the first openings 112. That is, as shown in FIG. 10, the first valve 210 blocks between the first openings 112 and the second openings 121

(e.g., as shown in FIG. 2) so that the first openings 112 are not connected to the second openings 121.

According to the aforementioned discussions, before the first valve 210 is closed, the first pistons 510 can create negative pressure at the first openings 112 to suck the remaining liquid in the first pipes 710 or the first channels 211. In the same manner, before the second valve 220 is closed, the second pistons 520 can create negative pressure at the fourth openings 114 to suck the remaining liquid in the second pipes 720 or the second channels 221. As such, there would be no remaining liquid in the first channels 211, the second channels 221, the first pipes 710 and the second pipes 720, such that it prevents the remaining liquid from contaminating another sample when the liquid processing module 10 is moved to the next testing position. In addition, the second pipes 720 are inclined and located close to openings of the liquid storage tanks 22, which helps to prevent liquid from splashing out while the liquid is injected into the liquid storage tanks 22.

According to the liquid processing module, the liquid testing system and the testing method as discussed above, before the valve is closed, the pistons can create negative pressure at the first openings or the fourth openings to suck the remaining liquid in the first channels, the second channels, the first pipes and the second pipes. As such, it prevents the remaining liquid from contaminating another sample while the liquid processing module is moved to the next testing position.

In addition, the second pipes are inclined and located close to the openings of the liquid storage tanks, which helps to prevent liquid from splashing out while the liquid is injected into the liquid storage tanks.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A liquid processing module, comprising:
    a base having a first groove and at least one first opening, the at least one first opening connected to the first groove;
    a first valve slidably located in the first groove; and
    at least one negative pressure generator configured to generate or remove negative pressure at the at least one first opening in response to the at least one first opening and the first groove being connected with each other.

2. The liquid processing module according to claim 1, wherein the base further has at least one first chamber, the at least one negative pressure generator comprises at least one first piston, and the at least one first piston is slidably located in the at least one first chamber.

3. The liquid processing module according to claim 2, wherein the base further has at least one second opening, the at least one second opening is connected to the at least one first opening through the first groove, the first valve has at least one first channel, the first valve is slidable between a first state and a second state with respect to the base; in response to the first valve being in the first state, the at least one first opening is connected to the at least one second opening through the at least one first channel; in response to the first valve being in the second state, the at least one first opening is not connected to the at least one second opening; and the at least one negative pressure generator is configured to generate or remove negative pressure at the at least one first opening in response to the first valve being in the first state.

4. The liquid processing module according to claim 3, further comprising a second valve, wherein the base further has a second groove, at least one third opening and at least one fourth opening, the at least one third opening and the at least one fourth opening are connected to the second groove, the second valve has at least one second channel, the second valve is located in the second groove and slidable between a third state and a fourth state; in response to the second valve being in the third state, the at least one third opening is connected to the at least one fourth opening through the at least one second channel; in response to the second valve being in the fourth state, the at least one third opening is not connected to the at least one fourth opening; and the at least one negative pressure generator is configured to generate or remove negative pressure at the at least one fourth opening in response to the second valve being in the third state.

5. The liquid processing module according to claim 4, wherein the base comprises a lower part and an upper part, the first groove and the second groove are located on the lower part, and the upper part covers the first groove and the second groove.

6. The liquid processing module according to claim 4, wherein the base comprises a lower part and an upper part, the first groove and the second groove are located on the upper part, and the lower part covers the first groove and the second groove.

7. The liquid processing module according to claim 4, wherein the base further has at least one second chamber, the at least one negative pressure generator further comprises at least one second piston, and the at least one second piston is slidably located in the at least one second chamber.

8. The liquid processing module according to claim 7, wherein the quantities of the at least one first chamber, the at least one first opening, the at least one second opening, the at least one first channel, the at least one first piston, the at least one second chamber, the at least one third opening, the at least one fourth opening, the at least one second channel and the at least one second piston are plural, and the first chambers, the first openings, the second openings, the first channels, the first pistons, the second chambers, the third openings, the fourth openings, the second channels and the second pistons are respectively arranged along a straight line.

9. The liquid processing module according to claim 4, further comprising two first seal rings, wherein the two first seal rings sleeve on the first valve, and are located on two opposite sides of the at least one first channel.

10. The liquid processing module according to claim 9, further comprising two second seal rings, wherein the two second seal rings are sleeved on the second valve and respectively located on two opposite sides of the at least one second channel.

11. The liquid processing module according to claim 4, further comprising a first pipe and a second pipe, wherein the first pipe is mounted on the first opening of the base, and the second pipe is mounted on the fourth opening of the base.

12. The liquid processing module according to claim 11, wherein the second pipe and the first pipe have an acute angle therebetween.

13. The liquid processing module according to claim 11, wherein a length of the first pipe that protrudes from the base is greater than a length of the second pipe that protrudes from the base.

14. The liquid processing module according to claim 4, further comprising a first driving component and a second driving component, wherein the first valve has a first assembling part, the second valve has a second assembling part, the first driving component comprises a first driving motor and a first stud, the first stud is rotatably mounted on the first driving motor, the first stud is screwed to the first assembling part, the first driving motor is configured to drive the first valve to slide with respect to the base, the second driving component comprises a second driving motor and a second stud, the second stud rotatably mounted on the second driving motor, the second stud is screwed to the second assembling part, and the second driving motor is configured to drive the second valve to slide with respect to the base.

15. A testing method, comprising:
opening a second valve to open a fourth opening;
injecting a first liquid into a liquid storage tank through the fourth opening;
generating negative pressure at the fourth opening;
closing the second valve to close the fourth opening;
opening a first valve to open a first opening;
sucking a second liquid located in the liquid storage tank through the first opening;
generating negative pressure at the first opening; and
closing the first valve to close the first opening.

16. A liquid testing system, comprising:
a testing stand;
a liquid processing module replaceably mounted on the testing stand, and the liquid processing module comprising:
a base having a first groove and at least one first opening which are connected to each other;
a first valve slidably located in the first groove; and
at least one negative pressure generator configured to generate or remove negative pressure at the at least one first opening in response to the at least one first opening and the first groove being connected with each other.

17. The liquid testing system according to claim 16, wherein the base further has at least one second opening, the at least one second opening is connected to the at least one first opening through the first groove, the first valve has at least one first channel, the first valve is slidable between a first state and a second state; in response to the first valve being in the first state, the at least one first opening is connected to the at least one second opening through the at least one first channel; in response to the first valve being in the second state, the at least one first opening is not connected to the at least one second opening; and the at least one negative pressure generator is configured to generate or remove negative pressure at the at least one first opening in response to the first valve being in the first state.

18. The liquid testing system according to claim 17, further comprising a liquid suction pump, wherein the liquid suction pump is disposed on the testing stand and connected to the at least one second opening.

19. The liquid testing system according to claim 17, further comprising a second valve, wherein the base further has a second groove, at least one third opening and at least one fourth opening, the at least one third opening and the at least one fourth opening are connected to the second groove, the second valve has at least one second channel, the second valve is slidably located in the second groove and slidable between a third state and a fourth state; in response to the second valve being in the third state, the at least one third opening is connected to the at least one fourth opening through the at least one second channel; in response to the second valve being in the fourth state, the at least one third opening is not connected to the at least one fourth opening; and the at least one negative pressure generator is configured to generate or remove negative pressure at the at least one fourth opening in response to the second valve being in the third state.

20. The liquid testing system according to claim 19, further comprising a liquid delivering pump, wherein the liquid delivering pump is disposed on the testing stand and connected to the at least one third opening.

* * * * *

UNITED STATES PATENT AND TRADEMARK OFFICE
CERTIFICATE OF CORRECTION

PATENT NO. : 11,420,199 B2
APPLICATION NO. : 16/057439
DATED : August 23, 2022
INVENTOR(S) : Chen-An Sung It is certified that error appears in the above-identified patent and that said Letters Patent is hereby corrected as shown below:

On the Title Page

In Column 1, insert:
-- (30) Foreign Application Priority Data
Mar. 21, 2018 (TW) ............ 107109688 --, therefor.

Signed and Sealed this
Twenty-fifth Day of October, 2022

Katherine Kelly Vidal
*Director of the United States Patent and Trademark Office*